United States Patent
Cartmell et al.

[11] Patent Number: 6,076,002
[45] Date of Patent: Jun. 13, 2000

[54] METHOD OF MANUFACTURING A DISPOSABLE ELECTRODE

[75] Inventors: James Vernon Cartmell, Xenia; Michael Lee Wolf, West Milton; Wayne Robert Sturtevant, Centerville, all of Ohio

[73] Assignee: NDM, Inc., Utica, N.Y.

[21] Appl. No.: 09/098,587

[22] Filed: Jun. 17, 1998

Related U.S. Application Data

[62] Division of application No. 08/767,671, Dec. 17, 1996.

[51] Int. Cl.⁷ ............................................. A61B 5/04
[52] U.S. Cl. ................... 600/372; 600/392; 600/397; 600/394; 607/149; 607/152; 29/592.1; 156/267; 156/268
[58] Field of Search ........................... 439/909; 606/32; 600/372, 382, 389, 386–397; 607/147, 152, 153; 29/592.1; 156/292, 248, 267, 268

[56] References Cited

U.S. PATENT DOCUMENTS

| | | |
|---|---|---|
| 3,976,055 | 8/1976 | Monter et al. . |
| 4,051,842 | 10/1977 | Hazel et al. . |
| 4,166,453 | 9/1979 | McClelland . |
| 4,178,052 | 12/1979 | Ekbom et al. . |
| 4,239,046 | 12/1980 | Ong . |
| 4,257,424 | 3/1981 | Cartmell . |
| 4,268,101 | 5/1981 | Stone . |
| 4,319,579 | 3/1982 | Cartmell . |
| 4,350,165 | 9/1982 | Striese . |
| 4,353,372 | 10/1982 | Ayer . |
| 4,367,755 | 1/1983 | Bailey . |
| 4,458,696 | 7/1984 | Larimore . |
| 4,635,642 | 1/1987 | Cartmell et al. . |
| 4,643,193 | 2/1987 | DeMarzo . |
| 4,653,501 | 3/1987 | Cartmell et al. . |
| 4,674,511 | 6/1987 | Cartmell . |
| 4,699,679 | 10/1987 | Cartmell et al. . |
| 4,721,111 | 1/1988 | Muttitt . |
| 4,727,881 | 3/1988 | Craighead et al. . |
| 4,763,660 | 8/1988 | Kroll et al. . |
| 4,773,424 | 9/1988 | Inoue et al. . |
| 4,797,125 | 1/1989 | Malana . |
| 4,827,939 | 5/1989 | Cartmell et al. . |
| 4,945,911 | 8/1990 | Cohen et al. . |
| 5,160,328 | 11/1992 | Cartmell et al. . |
| 5,195,523 | 3/1993 | Cartmell et al. . |
| 5,402,780 | 4/1995 | Faasse, Jr. . |
| 5,406,945 | 4/1995 | Riazzi et al. . |
| 5,429,589 | 7/1995 | Cartmell et al. . |
| 5,476,443 | 12/1995 | Cartmell et al. . |
| 5,501,661 | 3/1996 | Cartmell et al. . |
| 5,632,274 | 5/1997 | Quedens et al. . |
| 5,921,925 | 7/1999 | Cartmell et al. ................ 600/391 |

FOREIGN PATENT DOCUMENTS

| | | |
|---|---|---|
| 0029297 | 5/1981 | European Pat. Off. . |
| 0 194 823 | 9/1986 | European Pat. Off. . |
| 0217383 | 4/1987 | European Pat. Off. . |
| 0627193 | 12/1994 | European Pat. Off. . |
| WO 94/07409 | 4/1994 | WIPO . |
| WO 96/01077 | 1/1996 | WIPO . |

*Primary Examiner*—Linda C. M. Dvorak
*Assistant Examiner*—David Ruddy
*Attorney, Agent, or Firm*—Killworth, Gottman, Hagan & Schaeff, L.L.P.

[57] ABSTRACT

A biomedical electrode for an electrocardiograph or similar device is provided. The biomedical electrode includes a disposable electrode having an electrically conductive gel layer and a smooth layer film. The disposable electrode interfaces with a reusable leadwire connector having the relatively expensive metallic conductive material. The reusable leadwire adapter includes a vinyl top layer which attaches to the smooth layer film of the disposable electrode through surface attraction. The reusable leadwire adapter may include a suction cup which attaches to the disposable electrode through a partial vacuum. The reusable leadwire also includes a stud member which snaps into a standard leadwire connector.

11 Claims, 6 Drawing Sheets

METHOD OF MANUFACTURING A DISPOSABLE ELECTRODE

CROSS-REFERENCE TO RELATED APPLICATION

This is a divisional application of application Ser. No. 08/767,671 filed on Dec. 17, 1996 by Cartmell et al., entitled BIOMEDICAL ELECTRODE HAVING A DISPOSABLE ELECTRODE AND A REUSABLE LEADWIRE ADAPTER THAT INTERFACES WITH A STANDARD LEADWIRE CONNECTOR.

BACKGROUND OF THE INVENTION

The invention relates to the field of disposable biomedical electrodes for establishing an electrical connection between the skin of the human anatomy and an electromedical apparatus. More specifically, the present invention relates to a disposable biomedical electrode used in conjunction with a reusable leadwire adapter for an electrocardiograph or similar monitoring equipment.

Medical electrodes of the foregoing type are utilized in a number of applications for a variety of purposes. The monitoring is of physiological electric potentials to detect muscular activity of the heart muscle is generally well established, such apparatus being referred to in the art as electrocardiograph (also referred to herein as ECG) apparatus. The resulting traces derived from such apparatus provide a diagnostic tool for detecting heart disease and defects. Such monitoring of physiological electrical potentials may be employed in a number of other applications. However, the disposable biomedical electrode and reusable leadwire adapter of the present invention will be described herein with reference to their connection with ECG apparatus.

Such ECG traces may be desired in a number of different situations. For example, a simple ECG test to obtain a single tracing for diagnostic purposes may be carried out in a few minutes in a physician's office. Hence, medical electrodes utilized for such testing may be of a relatively simple disposable variety, since they are only in service for a very short time. Conversely, longer term monitoring applications require that the medical electrodes remain in place on the patient's skin for considerably extended periods of time. For example, in stress testing, the heart activity of the patient is monitored over a relatively longer period of time while the patient exercises on a tread mill or similar apparatus. Such testing may include monitoring of the heart activity during the exercise, as well as continued monitoring during the rest period thereafter so as to monitor the return of the heart to a normal or unstressed condition. Similarly, medical electrodes monitoring heart activity during surgery may be required to remain in place and operational for a period of several hours. In a similar fashion, patients hospitalized in an intensive care ward or other specialized care unit may require continuous, extended monitoring. Hence, medical electrodes utilized for long term ECG monitoring may be required to remain in service for many hours, and sometimes for many days.

Accordingly, there is a continuing need for high quality yet inexpensive medical electrodes for ECG and related uses which reliably transmit signals to enable traces to be obtained that accurately represent signals generated by the patient's heart. For purposes of convenience and safety, such medical electrodes should be inexpensive so that it is practical to dispose of them after only one use. In the past, an approach to providing inexpensive ECG medical electrodes has been to provide a disposable medical electrode which includes an electrolyte and a conductor engaged therein. For example, U.S. Pat. Nos. 4,773,424, 4,257,424, 4,643,193, 4,721,111 and 4,727,881 are all directed to disposable medical electrodes having an electrolyte and a conductor engaged therein.

It is generally recognized that, in order to obtain high quality, traces, the portion of the electrode conductor engaged in the electrolyte should be a conductive material. A biomedical electrode may include a first electrical conductor that is galvanically inactive in the presence of the electrolyte and a second electrical conductor that is galvanically active in the presence of the electrolyte. The second electrical conductor may consist of a minute particle of conductive material located at the interface between the first electrical conductor and the electrolyte. The minute particle of conductive material at the interface can be practically any metal that is galvanically active in the presence of the electrolyte. The metals or metal compounds present at the interface are preferably substantially pure. For example, U.S. Pat. No. 3,976,055, herein incorporated by reference, teaches that the galvanically active material may consist of numerous different types of metals and may be applied to the first electrical conductor by varying methods and quantities.

It is preferable that the conductive material in a biomedical electrode consist of either silver or a silver coated conductive plastic. When pure metallic silver is used, the electrolyte will preferably contain a chloride ion, thus forming a conductor coating commonly referred to in the art as a silver/silver chloride system. Such silver/silver chloride systems provide a regular electrocardiograph trace having a stable base line. The silver/silver chloride system eliminates the erratic traces and wandering base lines sometimes attributed to defibrillation. However, the silver/silver chloride part of the electrode is extremely expensive when compared to the costs associated with the other components of the medical electrode. There have been many attempts in the past to minimize the expense associated with silver/silver chloride systems used in medical electrodes. For example, U.S. Pat. No. 4,674,511 (commonly assigned) discloses a medical electrode for ECG monitoring which includes a conductor member comprising a thin strip of nonconductive material having a thin layer of electrically conductive paintable material adhered to one face thereof. By including only a thin strip of electrically conductive material on the medical electrode, the expense associated with such electrically conductive materials is minimized. However, the disposable medical electrode disclosed in U.S. Pat. No. 4,674,511 does in fact include the expensive electrically conductive material as a component and therefore, is discarded with the medical electrode. The disposition of the electrically conductive material increases the expense of using the disposable medical electrode.

As a response to such problems, attempts in the art have sought to provide a medical electrode having a reusable conductor portion. These medical electrodes typically comprise a disposable portion and a reusable conductor portion. For example, U.S. Pat. No. 4,653,501 (commonly assigned) discloses a medical electrode with a reusable conductor comprising a disposable electrode pad with a socket for receiving a reusable electrode conductor which is attached to a leadwire. The pad includes a socket plate having a release coated lower surface and a bore filled with a gel matrix which serves as the electrolyte contacting the patient's skin. In use, the medical electrode is applied to the skin of the patient and the releasable part of the clamp plates is peeled away from the socket plate. The electrode conductor is then inserted into the bore of the socket plate and the clamp is readhered to the socket plate in a covering relationship. The leadwire is then attached to the end such that the end of the leadwire and the electrode conductor are securely held in place relative to the electrolyte gel matrix.

Another attempt to minimize the expense of the medical electrode by incorporating a reusable conductor is disclosed in U.S. Pat. No. 4,635,642 (commonly assigned). The medical electrode comprises an electrode pad provided with a socket and a reusable electrode conductor which is attached to a leadwire. The electrode pad includes a laminated assembly of a pair of foamed sheets with an electrolyte gel matrix filling the gap between the foam sheets. An electrically nonconductive socket plate is disposed over the gel matrix and the foam sheets. The socket plate is provided with a socket or bore for receiving the reusable electrode conductor. The reusable electrode conductor has a ridged body slightly larger than the bore such that the bore resiliently engages the conductor. While these medical electrode assemblies may incorporate a reusable conductor, they are relatively expensive to manufacture in view of their complex structure as compared to other medical electrodes. Accordingly, medical electrodes having reusable conductors require a relatively sophisticated manufacturing scheme which significantly increases the cost of each medical electrode. Such costs substantially negate any savings associated with the reusable conductor feature.

Further, medical electrodes having reusable conductors in the prior art require non-standardized leadwires. Most hospitals and health care providers are equipped with standard leadwires which comprise a female portion of a snap fastener. The disposable electrode comprises the male portion of the snap fastener which snaps into the female portion of the standard leadwire. Non-standardized leadwires necessitate complete conversion within a hospital which is extremely difficult and expensive.

Accordingly, there remains a need in the art for a reusable leadwire adapter which is adaptable to standard leadwires; there is also a need for a disposable biomedical electrode assembly having a simple structure which is relatively inexpensive to manufacture; there is also a need for a biomedical electrode assembly which eliminates the expensive metallic conductive materials from the disposable portion of the biomedical electrode assembly so as to decrease the costs associated with use.

SUMMARY OF THE INVENTION

The present invention meets the aforementioned needs by providing a biomedical electrode requiring less expensive materials and which may be inexpensively manufactured. The biomedical electrode according to the present invention is used to interconnect a standard leadwire connector to a patient. The biomedical electrode comprises a disposable electrode and a reusable leadwire adapter. The disposable electrode is secured to the skin of a patient and serves to conduct the electrical signal between the patient and the reusable leadwire adapter. The reusable leadwire adapter has several functions. For example, the reusable leadwire adapter serves as the electrode sensor or conductor and as the interface between the disposable electrode and the standard leadwire connector. Additionally, the reusable leadwire adapter houses the electrode sensor or conductor. The combination of the disposable electrode and the reusable leadwire electrode, defined herein as the biomedical electrode, performs the medical electrode function of serving as a transducer between ionic and electric current flow. In this way, the reusable leadwire adapter is attached to the disposable electrode to provide a conductive path for the minute voltages generated by the patient's heart to the ECG apparatus. The biomedical electrode of the present invention provides a regular trace having a stable base line.

The disposable electrode of the present invention comprises a smooth layer film having an upper side, a lower side having an adhesive coating, and a first opening. Further, the disposable electrode includes a top layer having an upper side, a lower side having an adhesive coating, and a second opening corresponding to the first opening. The upper side of the top layer is secured to the lower side of the smooth layer film by means of the adhesive coating on the smooth layer film. Further, the disposable electrode includes an electrically conductive patch having an upper side and a lower side and comprising an electrically conductive gel layer and an anchoring layer formed of a porous material having sufficient porosity such that the anchoring layer is laminated on the electrically conductive gel layer. The upper side of the electrically conductive patch is secured to the lower side of the top layer by means of the adhesive coating on the top layer, and the lower side of the electrically conductive patch contacts a patient. The smooth layer film is preferably a polyethylene material and may include an adhesive coating on the upper side.

The lower side of the top layer includes a center portion and an outer portion. The electrically conductive patch is positioned within the center portion, and the outer portion of the top layer secures the electrode to the patient. Preferably, the adhesive coating on the lower side of the top layer is a patient-contact adhesive coating. Preferably, the electrically conductive gel layer is a hydrogel material.

According to another aspect of the current invention, the disposable electrode may comprise an electrical stabilizing strip having an upper side including an adhesive coating and a lower side. The electrically conductive gel patch has a center portion and an outer portion. A perforated portion of the anchoring layer is positioned on the upper side and within the center portion of the electrically conductive gel patch, and the upper side of the electrical stabilizing strip is secured on the lower side and within the center portion of the electrically conductive patch by means of the adhesive coating on the electrical stabilizing strip, such that the electrically conductive gel layer contacts the patient through the outer portion of the electrically conductive gel layer. The electrical stabilizing strip is an insulator, such as polyester material.

According to another aspect of the current invention, the disposable electrode preferably includes a release liner secured to the lower side of the top layer for protection of the disposable electrode prior to use. The lower side of the top layer has a pull tab, so as to provide a grippable surface to facilitate removal of the top layer from the release liner.

The reusable leadwire adapter for use with a standard leadwire connector according to a first embodiment of the present invention comprises a top layer having an upper side, a lower side having a reusable self-adhering surface, and a first opening. The reusable leadwire adapter includes a conductive terminal having a base portion integrally joined to a stud member. The base portion is mounted to the upper side of the top layer over the first opening. The stud member is sized to interface with the standard leadwire connector. A conductive eyelet is mounted to the lower side of the top layer over the first opening and electrically coupled to the base portion of the conductive terminal. The conductive terminal preferably includes at least one metallic particle, such as stainless steel. The conductive eyelet is preferably formed from a metallic material, such as silver. Preferably, the silver is chlorinated. The top layer can be composed of polyvinylchloride or polyurethane. According to another aspect of the current invention, the top layer may also include a smooth layer film positioned on the upper side of the top layer. The smooth layer film can be a polyethylene material.

The reusable leadwire adapter for use with a standard leadwire connector according to a second embodiment of the present invention comprises a suction cup top layer having an upper side, a lower side and a first opening. The reusable leadwire adapter includes a conductive terminal having a base portion integrally joined to a stud member. The base portion is mounted to the upper side of the suction cup top layer over the first opening. The stud member is sized to interface with the standard leadwire connector. A conductive eyelet is mounted to the lower side of the suction cup top layer over the first opening so that an air tight seal is formed between the conductive eyelet and the first opening. The conductive eyelet is electrically coupled to the base portion of the conductive terminal. Preferably, the lower side of the suction cup top layer includes a self-adhering film. The suction cup top layer may include a pull tab along an edge of the suction cup top layer. The conductive terminal preferably includes at least one metallic particle, such as stainless steel. The conductive eyelet is preferably formed from a metallic material, such as silver. Preferably, the silver is chlorinated. The top layer can be composed of polyvinylchloride or polyurethane. According to another aspect of the current invention, the top layer may also include a smooth layer film positioned on the upper side of the top layer. The smooth layer film can be a polyethylene material.

The biomedical electrode of the present invention comprises a reusable leadwire adapter which is reusable and which interfaces with a standard leadwire connector and a disposable electrode which is discarded after each use and which interfaces with the reusable leadwire adapter and a patient. The disposable electrode includes a smooth layer top film. The reusable leadwire adapter includes a bottom layer having a reusable self-adhering surface according to the first embodiment of the present invention. The reusable leadwire adapter interfaces with the disposable electrode through surface attraction between the smooth layer film and the reusable self-adhering surface. According to the second embodiment of the present invention, the top layer of the reusable leadwire adapter includes a suction cup top layer, such that the reusable leadwire adapter interfaces with the disposable electrode through a partial vacuum between the suction cup top layer and the disposable electrode. The reusable leadwire adapter may include the reusable self-adhering surface and the disposable electrode may include the smooth layer film for additional adhesion.

A method of manufacturing the disposable electrode according to the present invention comprises the steps of: a) providing a smooth layer film having an upper side and a lower side having an adhesive coating; b) providing a top layer having an upper side and a lower side having an adhesive coating; c) applying the lower side of the smooth layer film to the upper side of the top layer by means of the adhesive coating on the smooth layer film; d) punching a hole in the smooth layer film and the top layer; e) providing an electrically conductive gel web having an upper side and a lower side and comprising an electrically conductive gel layer and an anchoring layer formed of a porous material having sufficient porosity such that the anchoring layer is laminated on the electrically conductive gel layer; and f) applying the upper side of the electrically conductive web to the lower side of the top layer by means of the adhesive coating on the top layer. The smooth layer film is preferably a polyethylene material. The upper surface of the smooth layer film may also include an adhesive coating. The lower side of the top layer may also includes a center portion and an outer portion with the electrically conductive patch positioned over the center portion. The electrically conductive gel layer is preferably a hydrogel. Preferably, the electrically conductive gel web has a center portion and an outer portion. The perforated portion of the anchoring layer is positioned on the upper side and over the center portion of the electrically conductive gel web. In accordance with another aspect of the present invention, the method further comprises the steps of: g) providing an electrical stabilizing strip having an adhesive coating; and h) applying the electrical stabilizing strip to the lower side and over the center portion of the electrically conductive gel web by means of the adhesive coating on the electrical stabilizing strip. Preferably, the electrical stabilizing strip is an insulator, such as polyester. In accordance with yet another aspect of the present invention, the method comprises the step of applying a release liner to the lower side of the top layer. The lower side of the top layer may also have a pull tab, so as to provide a grippable surface to facilitate removal of the disposable electrode from the release liner. In accordance with yet another aspect of the present invention, the method comprises the step of cutting the disposable electrode to a desired shape. In accordance with yet another aspect of the present invention, the method comprises the step of making a separation cut between successive disposable electrodes.

A major portion of the cost savings arise by virtue of the reusable lead wire connector including as a component the relatively expensive metallic conductive material. In the past, the disposable portion of the electrode included the metallic conductive material such as the silver/silver chloride system, which was discarded after a single use. This significantly added to the cost of using each electrode. Past attempts in the art have incorporated the conductive material in a reusable non-standard leadwire connector. However, hospitals and health care providers have been reluctant to replace standard leadwire connectors. The present invention provides a solution by incorporating the conductive material in a reusable leadwire adapter which interfaces with a standard leadwire connector, thereby eliminating the expensive metallic conductive material from disposable portion of the electrode. Other objects and advantages of the invention will be apparent from the following description, the accompanying drawings and the appended claims.

Note: All Figures are illustrative and not drawn to scale.

DETAILED DESCRIPTION OF THE PREFERRED EMBODIMENTS

Figure 1:
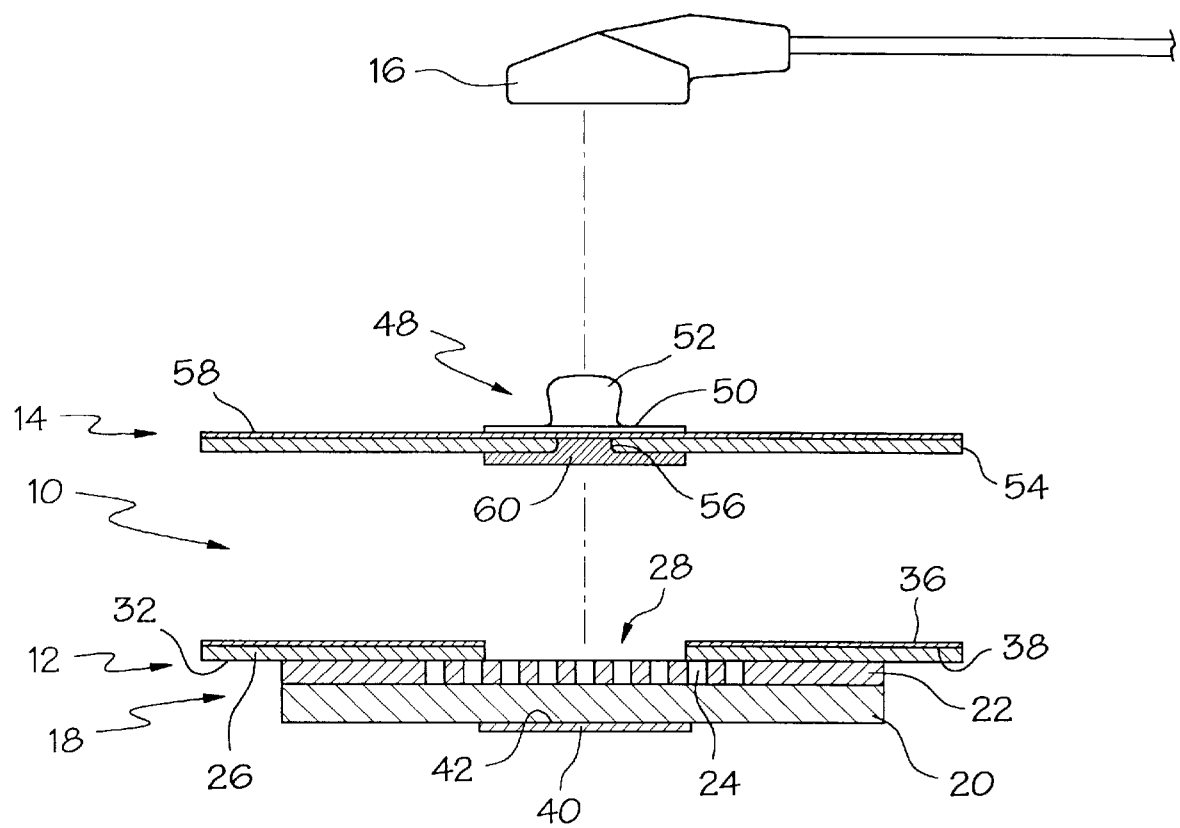
FIG. 1 is a schematic view of a biomedical electrode in accordance with a first embodiment of the present invention.

Referring now to FIG. 1, a biomedical electrode 10 which comprises a disposable electrode 12 and a reusable leadwire adapter 14 is shown in accordance with a first embodiment of the present invention. The disposable electrode 12 will be discarded after a single use while reusable leadwire adapter 14 will be used repeatedly. The disposable electrode 12 may be secured directly to the skin of a patient requiring ECG monitoring. The reusable leadwire adapter 14 interfaces with a standard leadwire connector 16 and the disposable electrode 12. The standard leadwire connector 16 is used by most hospitals and health care providers. The standard leadwire connector 16 comprises the female portion of a snap connector (not shown). The standard leadwire connector 16 snaps onto a correspondingly configured male portion of a snap connector and transmits generated ECG signals to a processing device (not shown) for display and interpretation.

Figure 2:
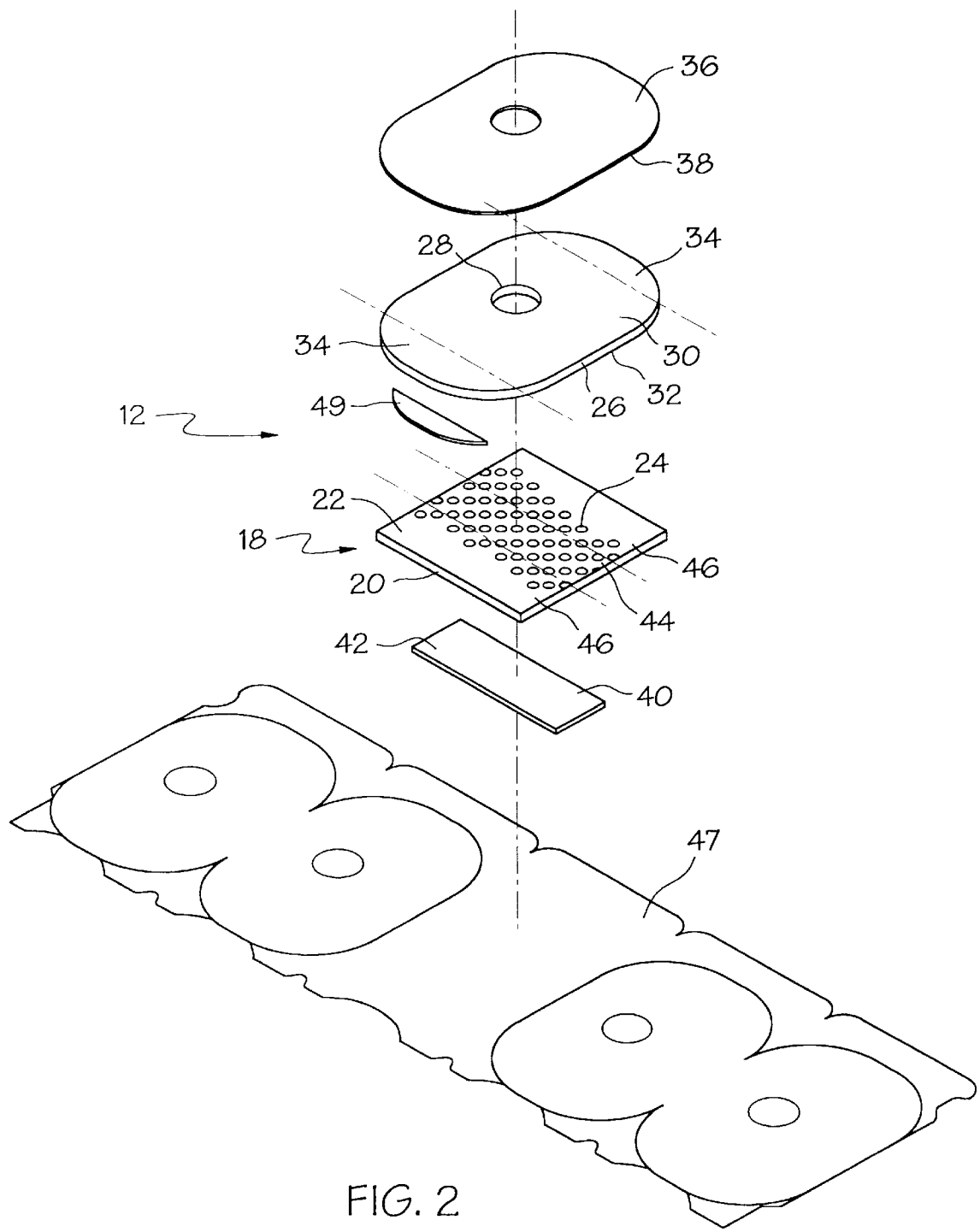
FIG. 2 is an exploded view of the disposable electrode in accordance with the present invention.

Referring to FIGS. 1 and 2, the disposable electrode 12 does not include any metallic conductive material. Rather, disposable electrode 12 comprises an electrically conductive gel patch 18 comprising an electrically conductive gel layer 20 laminated to an anchoring layer 22 having a perforated portion 24. The anchoring layer 22 is formed of a porous material having sufficient porosity such that anchoring layer 22 can be secured to gel layer 20 without an adhesive. It has been found that when anchoring layer 22 is formed of sufficiently porous material, it readily adheres to most conventional electrically conductive gels, such as electrolytic gels and hydrogels. Other materials do not adhere directly to electrolytic gels and, thus, require an adhesive coating in order to provide a means by which the anchoring layer 22 can be secured to gel layer 20. Prior art gel layers included support layers of cloth secured by means of an adhesive. The support layer facilitated handling of the gel layer during processing. However, anchoring layer 22 possesses sufficient porosity to eliminate the necessity of an adhesive and support layer, thereby reducing cost of electrode 12 by reducing material and manufacturing expenses. The perforated portion 24 may be formed by punching perforations in the material used to form the anchoring layer 22. However, it will be appreciated by those skilled in the art that the perforated portion 24 may be an inherent quality of the material used to form the anchoring layer 22. The material may be of such porosity that a conductive path is formed through the anchoring layer 22 as the gel material permeates completely through the interstices of the anchoring layer material.

Preferably, anchoring layer 22 is formed of a porous material comprising a foam material including silica and a polyoelfin, wherein the porous material has a porosity ranging from about 30% to about 80%. The preferred porous material is a microporous synthetic sheet commercially available from PPG Industries, Inc. under the trademark Teslin®. Those skilled in the art will understand that the extent to which the porous material must be porous will depend upon the particular gel material chosen to form gel layer 20. Further, those skilled in the art will appreciate that sufficiently porous materials other than those described herein may be used without departing from the scope of the invention. Finally, those skilled in the art will appreciate that the degree to which the gel material permeates the anchoring layer 22 will depend on the materials chosen and the porosity of the anchoring layer 22.

Further, disposable electrode 12 includes a top layer 26 having an opening 28 located within the center portion 30 of top layer 26. The lower surface or side of top layer 26 preferably includes a patient-contact adhesive coating 32. The lower surface of top layer 26 is adhesively mounted to anchoring layer 22 of electrically conductive patch 18.

Preferably, top layer 26 is oblong shaped having a center portion 30 and an outer portion 34. Electrically conductive patch 18 is positioned within center portion 30 of top layer 26 and over opening 28 such that the remaining outer portion 34 of top layer 26 secures disposable electrode 12 to the patient. Outer portion 34 is sized to provide sufficient contact between disposable electrode 12 and the patient's skin. Further, the perforated potion 24 of anchoring layer 22 is positioned over opening 28 to allow electrical contact between gel layer 20 and reusable leadwire adapter 14. Further, those skilled in the art will appreciate that top layer 24 may have any shape that is compatible with the patient and reusable leadwire adapter 14. For example, top layer 24 may also be circular, oval, square or rectangular. Preferably, top layer 26 may be formed of a polymeric film material such as polyethylene, polyester or the like, as well as other flexible semi-rigid materials. In addition, the top layer 26 may be formed of a foam, film or cloth material.

Further, disposable electrode 12 comprises a smooth layer film 36 having opening 28. Preferably, the lower surface or side of smooth layer film 36 includes an adhesive 38. Smooth layer film 36 is adhesively mounted to the upper surface or side of top layer 26. Smooth layer film 36 is preferably made from a nonconductive material, such as polyethylene.

Additionally, disposable electrode 12 may comprise an electrical stabilizing strip 40. Preferably, the upper surface or side of electrical stabilizing strip 40 includes an adhesive 42. Electrical stabilizing strip 40 is adhesively mounted to the lower surface or side of electrically conductive gel patch 18. Electrical stabilizing strip 40 is positioned over the center portion 44 of gel patch 18 such that the electrically conductive gel layer 20 makes contact with the patient through the outer portion 46 of gel patch 18. Electrical stabilizing strip 40 is wider than said opening 28 but narrower than gel patch 18. Electrical stabilizing strip 40 is made from an insulating material, such as polyester.

Figure 3:
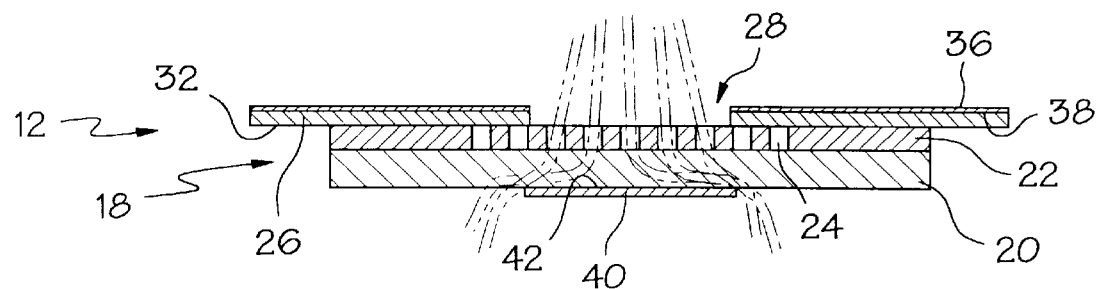
FIG. 3 is a side view of the disposable electrode illustrating the signal blocking function of the electrical stabilizing strip.

Electrical stabilizing strip 40 blocks direct electrical contact between the patient's skin and reusable leadwire adapter 14. Blocking direct electrical contact reduces the noise that is produced when the patient moves or when a nurse adjusts disposable electrode 12. All signals are forced to travel around electrical stabilizing strip 40, as shown in FIG. 3, through at least some portion of the gel layer 20. Any shifting of disposable electrode 12 caused by patient movement will have a minimal effect on any generated signals since the signals must travel around electrical stabilizing strip 40 to reusable leadwire adapter 14. Electrical stabilizing strip 40 is important for electrodes used for long term monitoring and stress testing since the patient is physically active. The effects of noise caused by patient movement can be reduced leading to higher quality traces.

FIG. 2 also illustrates a release liner 47. Release liner 47 is secured to the lower surface or side of top layer 26 to protect disposable electrode 12 prior to use. Release liner 47 helps prevent gel layer 20 from drying out and prevents contamination of patient-adhesive coating 32 and the gel layer 20. An optional pull tab 49 may be secured to the outer portion 34 of top layer 26. When pull tab 49 is used in conjunction with release liner 47, the user can simply peel disposable electrode 12 away from liner 47 by grasping pull tab 49. Thereafter, the user can remove the pull tab 49 and mount disposable electrode 12 on the patient. Such techniques are conventional and well known. The pull tab 49 and the release liner 47 may be composed of any one of a number of materials, such as silicone-coated paper.

Figure 4:
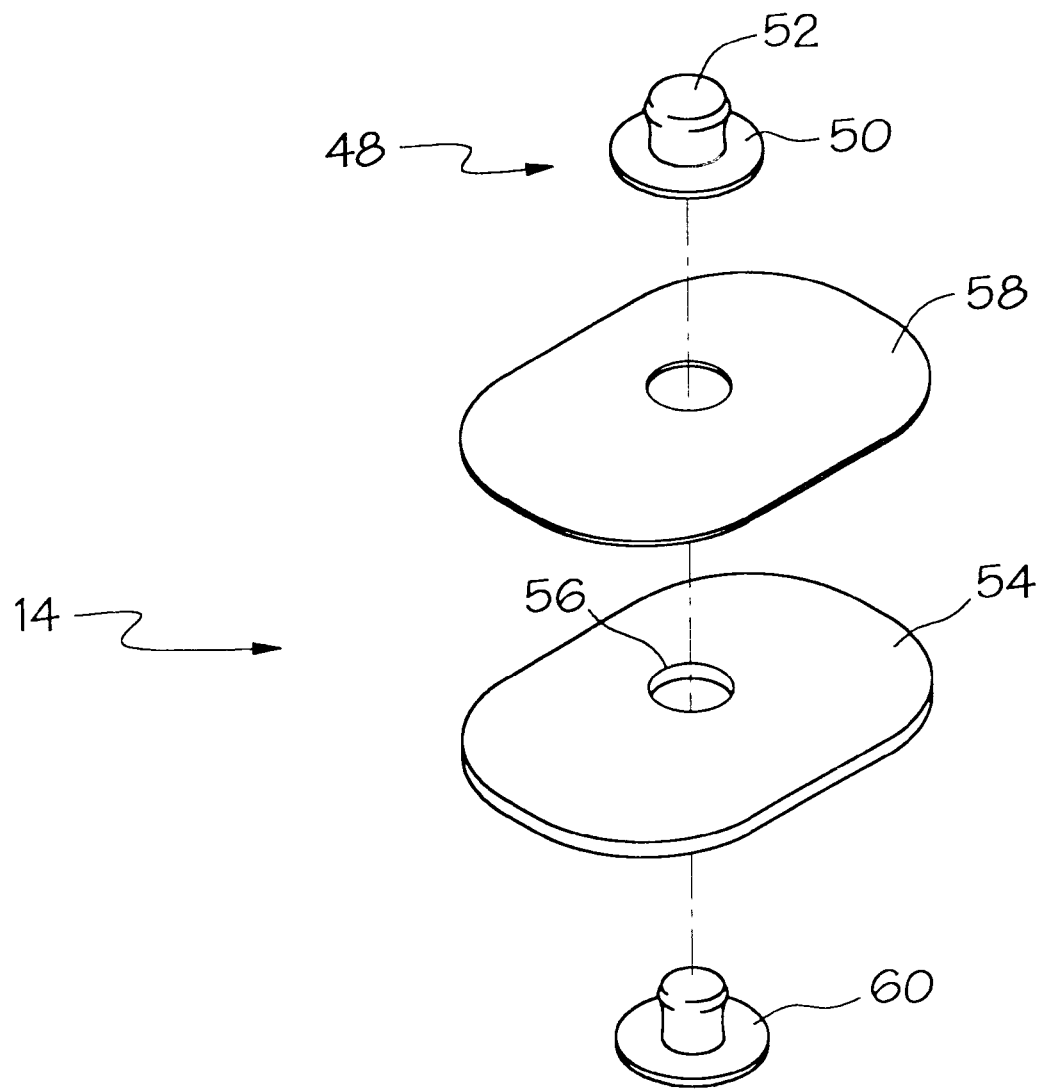
FIG. 4 is an exploded view of the reusable leadwire adapter in accordance with the first embodiment of the present invention.

According to a first embodiment of the present invention, reusable leadwire adapter 14 is designed to interface with standard leadwire connector 16 and disposable electrode 12 as shown in FIG. 1. Referring to FIGS. 1 and 4, the reusable leadwire adapter 14 includes a conductive terminal 48 comprising a base portion 50 integrally joined to a stud member 52. Stud member 52 is sized and shaped to snap into any standard leadwire connector 16. Base portion 50 is positioned on the upper surface or side of top layer 54. Conductive terminal 48 may be formed of any conductive material. Conductive terminal 48 is preferably formed of a metallic material, such as stainless steel, or is provided with a metallized outer layer, but it can comprise other materials such as conductive carbon interdispersed in a thermoset carbon. It will be appreciated by those skilled in the art that other conductive materials may be used to form conductive terminal 48.

Top layer 54 has an opening 56 and an optional thin layer film 58. Preferably, thin layer film 58 is made from a nonconductive material selected from the group consisting of polyethylene terephthalate (commercially available from E. I. DuPont de Nemours & Co. under the trademark Mylar®), polystyrene, polyethylene, polypropylene and polyvinylchloride. The most preferable nonconductive material is polyethylene. Thin layer film 58 may be printed to improve the esthetics of reusable leadwire adapter 14.

Opening 56 is correspondingly sized with stud member 52. Base portion 50 is wider than opening 56 and completely covers the opening. Opening 56 is preferably located near the center portion of top layer 54. Top layer 54 may have any shape that is compatible with the patient and disposable electrode 12. For example, top layer 54 may be circular, oval, oblong, square or rectangular. Preferably, top layer 24 is oblong to correspond with the shape of preferred disposable electrode 12. However, it will be appreciated by those skilled in the art that reusable leadwire adapter 14 and disposable electrode 12 may have different shapes and still function as intended.

Further, reusable electrode adapter 14 comprises a conductive eyelet 60 positioned on the lower surface or side 55 of top layer 54. Conductive eyelet 60 has a generally flat lower surface 60a. Preferably, opening 28 is sized slightly larger than the diameter of conductive eyelet lower surface 60a so that the lower surface 60a of conductive eyelet 60 makes complete contact with gel layer 20 and anchoring layer 22 of disposable electrode 12 through opening 28. Conductive eyelet 60 is electrically coupled to base portion 50 of conductive terminal 48 through opening 56. Conductive eyelet 60 protrudes through opening 56 and securely fastens conductive terminal 48 to top layer 54. Conductive eyelet 60 may be friction fitted, riveted or crimped into conductive terminal 48. An adhesive may also be used to fasten conductive terminal 48 to the upper surface of top layer 54 and conductive eyelet 60 to the lower surface of top layer 54.

Preferably, conductive eyelet 60 is formed of a metallic material, such as silver, with a chlorinated outer surface. Conductive eyelet can be formed of solid silver which would be very expensive. As discussed previously, only a minute amount of silver is needed to yield high quality traces. Nonconductive materials, such as nylon, can be made conductive by inclusion of carbon, and plated or coated with at least one particle of silver. It is also possible to use silver plated non-conductive material to yield high quality traces. While silver is the preferred metallic material, other metals, such as stainless steel or zinc, may also be used. See U.S. Pat. No. 3,976,055, incorporated by reference, for additional types of metals and the manner in which they can be applied. The conductive material used should also be compatible with the electrically conductive gel layer in the disposable electrode. Silver with a chlorinated outer surface is compatible with most electrically conductive gel layers currently used and preferred for long term monitoring applications.

Correspondingly, it is preferable to have a gel layer 20 which is a hydrogel material formed from an aqueous mixture of polyhydric alcohol, an aliphatic diisocyanate-terminated prepolymer, polyethylene oxide-based diamine, and sodium chloride. It should be understood that hydrogels other than those described herein which have the desired properties may be used as gel layer 20 without departing from the scope of the invention. Preferably, the polyhydric alcohol is selected from the group consisting of polypropylene glycol, polyethylene glycol and glycerine. The resulting hydrogel material is an electrically conductive and highly absorbent material capable of retaining large amounts of fluid, thereby rendering it very moist and soothing. By forming the hydrogel material from the aforementioned aqueous mixture, it remains intact and experiences minimal "dry-out" problems, even over extended storage periods.

Moreover, the hydrogel used to form gel layer 20 does not adhere or stick to the patient's body, thereby allowing for easy removal of disposable electrode 12 substantially as a single piece and without adhering to the patient's hair. Additionally, the biocompatibility of the hydrogel is extremely favorable and, therefore, provides a biocompatible, non-irritating, fluid-absorbing, bacterial-protective, cushioning, skin-like media in and over the patient's skin during monitoring.

Those skilled in the art will appreciate that a wide variety of aliphatic diisocyanates may be used in accordance with the invention including but not limited to hexamethylene diisocyanate, isophoronediisocyanate, tetramethylene diisocyanate, and decamethylene diisocyanate. The preferred aliphatic diisocyanate-terminated prepolymer, however, is an isophoronediisocyanate-terminated prepolymer based on polyols containing more than about 40% polyethylene oxide and having an isocyanate content of about 3% by weight. The molecular weight of the isophoronediisocyanate-terminated prepolymer is preferably, from about 1500 to about 8000 and, most preferably, from about 4000 to 5000. The polyethylene oxide-based polyamine is preferably a polyethylene oxide-based diamine having a molecular weight in a range from about 200 to about 6000 and, most preferably about 2000. It is also preferable that the aliphatic diisocynate-terminated prepolymer and the polyethylene oxide-based polyamine have a stoichiometric ratio of about 1:1. Those skilled in the art will appreciate that all of the constituents of the preferred hydrogel material may be readily synthesized or purchased commercially, with neither method preferred over the other.

It has also been found that a more preferred hydrogel material is formed from an aqueous mixture including from about 0% to about 90% by weight polyhydric alcohol; from about 6% to about 60% by weight aliphatic diisocyanate-terminated prepolymer; from about 4% to about 40% by weight polyethylene oxide-based polyamine; up to about 2% by weight sodium chloride; and the balance water. A more preferred hydrogel composition for forming the hydrogel material is formed from a mixture comprising from about 15% to about 30% by weight polypropylene glycol; from about 8% to about 14% by weight isophoronediisocyanate-terminated prepolymer; from about 5% to 10% by weight polyethylene oxide-based diamine; up to about 1% by weight sodium chloride; and the balance water. Most preferably, the hydrogel material is formed from a mixture comprising: (a) from about 16% to 17% by weight polypropylene glycol; (b) from about 10% to 12% by weight isophoronediisocyanate-terminated prepolymer; (c) from about 7% to 9% by weight polyethylene oxide-based diamine; (d) from about 0.5% to 1% by weight sodium chloride; and (e) the balance water.

Preferably, a lower surface 55 of top layer 54 is tacky to the touch according to the first embodiment of the present invention. Top layer 54 may be composed of polyurethane, polyvinylchloride or other soft rubber-like materials. For example, one such material is commercially available from 3M, Inc. under the trademark, Cling Vinyl®. Cling Vinyl® comprises a reusable self-adhering film. The lower surface 55 of top layer 54 interfaces with the upper surface of smooth layer film 36 through surface attraction. The surface attraction between the Cling Vinyl® top layer 54 and the polyethylene smooth layer film 36 firmly secures reusable leadwire adapter 14 to disposable electrode 12. It will be appreciated by those skilled in art, that other materials with a tacky surface may be used. It will be further appreciated by those skilled in the art that the tacky surface may be a property of the material used for the top layer 54 or a separate layer added to the top layer 54.

Figure 7:
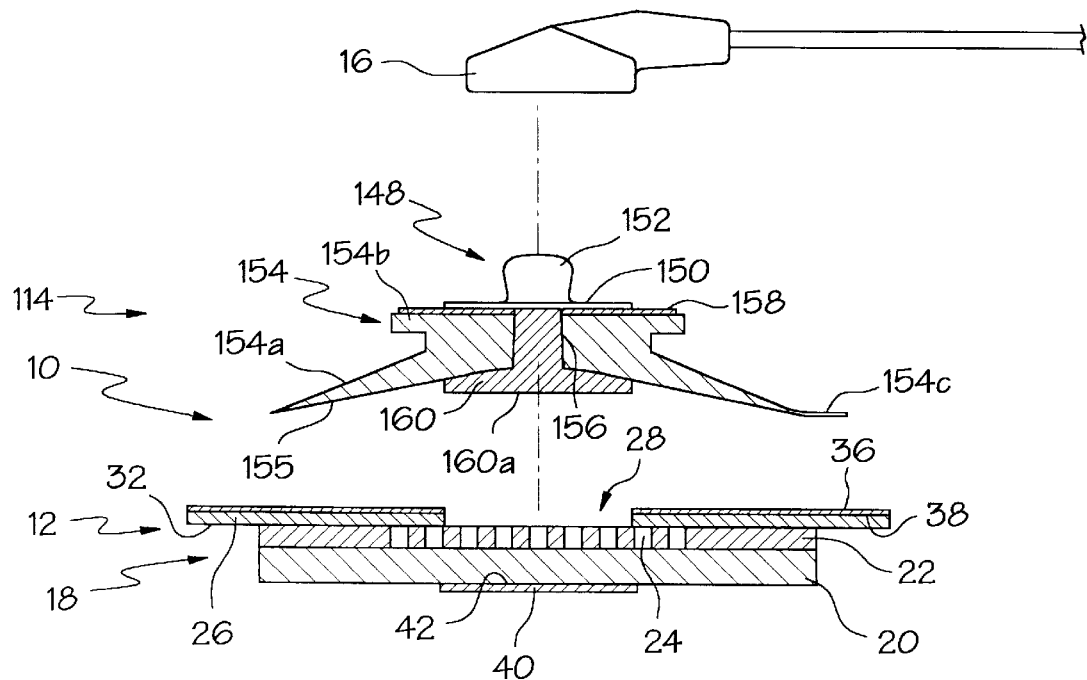
FIG. 7 is a schematic view of a biomedical electrode in accordance with a second embodiment of the present invention.
Figure 8:
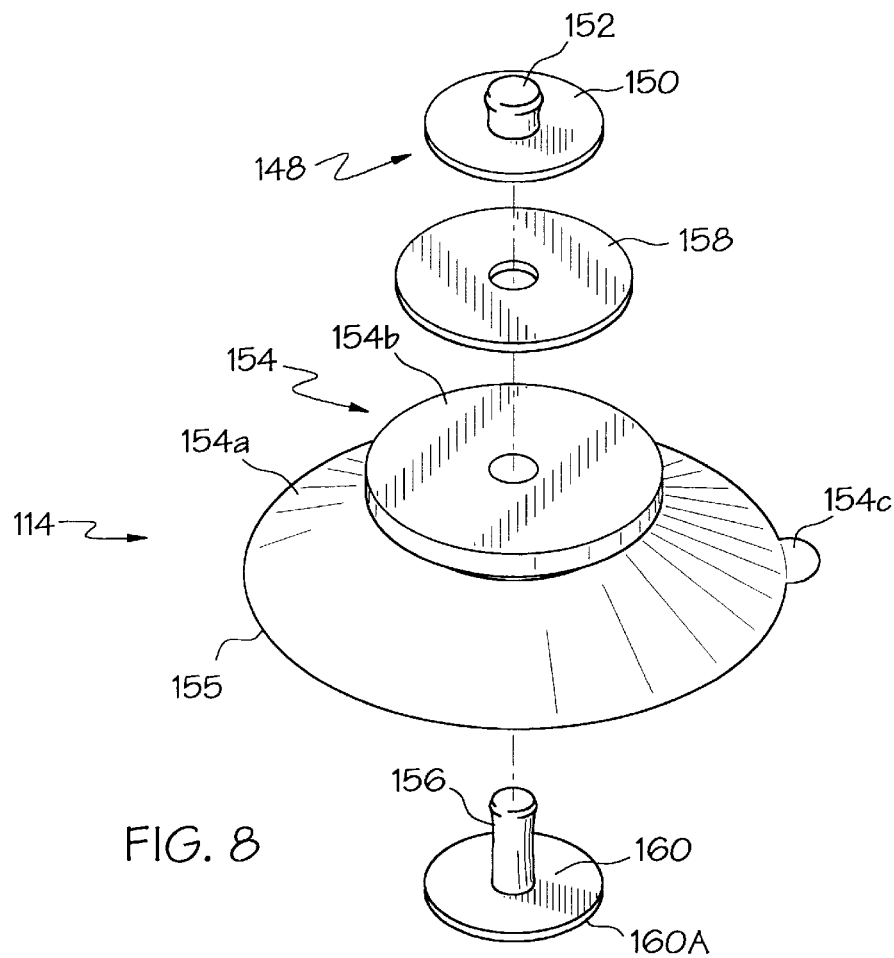
FIG. 8 is an exploded view of the reusable leadwire adapter in accordance with the second embodiment of the present invention.

Referring now to FIG. 7, a biomedical electrode 10 which comprises the disposable electrode 12 and a reusable leadwire adapter 114 is shown in accordance with a second embodiment of the present invention. The reusable leadwire adapter 114 is designed to interface with the disposable electrode 12 as in the first embodiment of the invention. Referring to FIGS. 7 and 8, the reusable leadwire adapter 114 includes a suction cup top layer 154 having a cup shaped portion 154a, a generally planar base portion 154b and a tab portion 154c. Tab portion 154c is positioned along an edge of cup shaped portion 154a and is used to remove the reusable leadwire adapter 114 from the disposable electrode 12 as desired. The reusable leadwire adapter 114 includes a conductive terminal 148 comprising a base portion 150 integrally joined to a stud member 152. Stud member 152 is sized and shaped to snap into any standard leadwire connector 16. Base portion 150 is positioned on the upper surface or side of base portion 154b of suction cup top layer 154. Conductive terminal 148 may be formed of any conductive material. Conductive terminal 148 is preferably formed of a metallic material, such as stainless steel, or is provided with a metallized outer layer, but it can comprise other materials such as conductive carbon interdispersed in a thermoset carbon. It will be appreciated by those skilled in the art that other conductive materials may be used to form conductive terminal 148.

Suction cup top layer 154 has an opening 156 through base portion 154b and cup shaped portion 154a and an optional thin layer film 158. Preferably, thin layer film 158 is made from a nonconductive material selected from the group consisting of polyethylene terephthalate (commercially available from E. I. DuPont de Nemours & Co. under the trademark Mylar®), polystyrene, polyethylene, polypropylene and polyvinylchloride. The most preferable nonconductive material is polyethylene. Thin layer film 158 may be printed to improve the esthetics of reusable leadwire adapter 114.

Opening 156 is corresponding sized with stud member 152. Base portion 150 is wider than opening 156 and completely covers the opening. Opening 156 is preferably located near the center portion of suction cup top layer 154. Preferably, suction cup top layer 154 is generally circular. It will be appreciated by those skilled in the art that suction cup top layer 154 may have any shape that is compatible with the patient and disposable electrode 12. However, it will be appreciated by those skilled in the art that reusable leadwire adapter 114 and disposable electrode 12 may have different shapes and still function as intended.

Further, reusable electrode adapter 114 comprises a conductive eyelet 160 positioned on the lower surface or side 155 of the cup shaped portion 154a of suction cup top layer 154. Conductive eyelet 160 has a generally flat lower surface 160a. Preferably, opening 28 is sized slightly larger than the diameter of the conductive eyelet lower surface 160a so that the lower surface 160a of conductive eyelet 160 makes complete contact with gel layer 20 and anchoring layer 22 of disposable electrode 12 through opening 28. Conductive eyelet 160 is electrically coupled to base portion 150 of conductive terminal 148 through opening 156. Conductive eyelet 160 protrudes through opening 156 and securely fastens conductive terminal 148 to suction cup top layer 154. Conductive eyelet 160 may be friction fitted, riveted or crimped into conductive terminal 148. An adhesive may also be used to fasten conductive terminal 148 to the upper surface of suction cup top layer 154 and conductive eyelet 160 to the lower surface 155 of suction cup top layer 154. The conductive eyelet 160 is secured to conductive terminal 148 so that there is an air tight seal between conductive eyelet 160 and opening 156. Preferably, suction cup top layer 154 is composed of polyurethane, polyvinylchloride or other soft rubber-like materials. A soft rubber-like material enables an air tight seal to be formed since the soft rubber-like material acts as an o-ring between conductive eyelet 160 and opening 156.

Preferably, conductive eyelet 160 is formed of a metallic material, such as silver, with a chlorinated outer surface. Conductive eyelet can be formed of solid silver which would be very expensive. As discussed previously, only a minute amount of silver is needed to yield high quality traces. Nonconductive materials, such as nylon, can be made conductive by inclusion of carbon, and plated or coated with at least one particle of silver. It is also possible to use silver plated non-conductive material to yield high quality traces. While silver is the preferred metallic material, other metals, such as stainless steel or zinc, may also be used. See U.S. Pat. No. 3,976,055, incorporated by reference, for additional types of metals and the manner in which they can be applied. The conductive material used should also be compatible with the electrically conductive gel layer in the disposable electrode. Silver with a chlorinated outer surface is compatible with most electrically conductive gel layers currently used and preferred for long term monitoring applications.

The lower surface 155 of suction cup top layer 154 interfaces with the upper surface of smooth layer film 36 through a partial vacuum. A partial vacuum is formed by compressing the suction cup top layer 154 against the smooth layer film 36 of disposable electrode 12. Excess air is forced out and the seal between the cup shaped portion 154a and the smooth layer film 36 forms a partial vacuum. The lower surface 155 is substantially flatten against the upper surface of smooth layer film 36 as the partial vacuum is formed. For additional adhesion, the lower surface 155 may include the same self-adhering film as the reusable leadwire adapter 14 of the first embodiment. Thus, the disposable electrode 12 and the reusable leadwire adapter 114 are secured together through surface attraction and a partial vacuum. Therefore, it is preferable that the reusable leadwire adapter 114 be formed of a similar tacky material as the reusable leadwire adapter 14 of the first embodiment.

The biomedical electrode according to the first embodiment is used as follows. The user snaps standard leadwire connector 16 to stud member 52 of the reusable leadwire adapter 14. Disposable electrode 12 is removed from release liner 48 and placed on the patient's skin. Reusable leadwire adapter 14 is placed on top of disposable electrode 12 so that conductive eyelet 60 contacts gel layer 20 through anchoring layer 22 and opening 28. Alternatively, reusable leadwire adapter 14 may be placed on top of disposable electrode 12 and then snapped into standard leadwire 16. The order of placement is not critical as long as conductive eyelet 60 contacts gel layer 20 and stud member 52 snaps into standard leadwire connector 16. Surface attraction between top layer 54 and smooth film layer 36 keeps reusable leadwire adapter 14 secured to disposable electrode 12. The surface attraction is sufficient to keep the biomedical electrode 10 secured in place during long term monitoring and stress testing applications in which the patient is active.

After monitoring is concluded, reusable leadwire adapter 14 is separated from disposable electrode 12 by simply peeling away at the interface. Disposable electrode 12 is removed from the patient and thrown away. The lower surface 55 of top layer 54 of reusable leadwire adapter 14 is simply wiped clean with a damp cloth, if necessary, and the reusable leadwire adapter 14 is then ready for reuse. The use of material with a tacky surface alleviates any special storage requirements for reusable leadwire adapter 14 since it simply has to be wiped clean with a damp cloth prior to use.

The biomedical electrode according to the second embodiment is used as follows. The user snaps standard leadwire connector 16 to stud member 152 of the reusable leadwire adapter 114. Disposable electrode 12 is removed from release liner 48 and placed on the patient's skin. Reusable leadwire adapter 114 is placed on top of disposable electrode 12 so that conductive eyelet 160 contacts gel layer 20 through anchoring layer 22 and opening 28. Reusable leadwire adapter 114 is compressed so that a partial vacuum is formed between the cup shaped portion 154a and the disposable electrode 12. The lower surface 155 of cup shaped portion 154a is substantially flattened against the upper surface of the smooth layer film 36 as the partial vacuum is formed so that the lower surface 160a of conductive eyelet 160 contacts the gel layer 20 through anchoring layer 22 and opening 28. Alternatively, reusable leadwire adapter 114 may be placed on top of disposable electrode 12 and then snapped into standard leadwire 16. The order of placement is not critical as long as conductive eyelet 160 contacts gel layer 20 and stud member 152 snaps into standard leadwire connector 16. The partial vacuum keeps the reusable leadwire adapter 114 secured to the disposable electrode 12.

If the reusable leadwire adapter 114 is formed of a similar tacky material as reusable leadwire adapter 14, the partial vacuum and surface attraction between suction cup top layer 154 and smooth film layer 36 keep reusable leadwire adapter 114 secured to disposable electrode 12. While the partial vacuum is sufficient to keep the reusable leadwire adapter 114 secured to the disposable electrode 12, surface attraction increases the adhesion between the reusable leadwire adapter 114 and disposable electrode 12.

After monitoring is concluded, reusable leadwire adapter 114 is separated from disposable electrode 12 by grasping pull tab 154c and peeling away at the interface. Disposable electrode 12 is removed from the patient and thrown away. The reusable leadwire electrode 114 may be simply wiped clean with a damp cloth or sterilized using standard hospital procedures. If the reusable leadwire adapter 114 is formed of a similar tacky material as the reusable leadwire electrode 14 of the first embodiment, the lower surface 155 of cup shaped portion 154a of reusable leadwire adapter 114 is simply wiped clean with a damp cloth, if necessary, and the reusable leadwire adapter 114 is then ready for reuse.

Reusable leadwire adapter 14, 114 lasts as long as a standard leadwire connector, which is six months to a year. Disposable electrode 12 contains no metallic material so the cost of manufacturing is reduced. Reusable leadwire adapter 14, 114 contains the relatively expensive metallic materials but may be reused so the long term costs drop. The cost of the relatively expensive metallic materials is spread over a larger number of monitoring events such that the per use cost is less. Further, disposable electrode 12 and reusable leadwire adapter 14, 114 are used in the same manner as current monitoring electrodes such that user retraining is not required. Finally, reusable leadwire adapter 14, 114 is designed to interface with standard leadwires such that hospitals do not have to buy new leadwires.

Other materials may be used in place of Cling Vinyl® and polyethylene smooth layer film. As will be appreciated by those skilled in the art, other materials with similar surface attraction characteristics may be used without deviating from the intended scope of the invention. For example, a light adhesive may be added to the upper surface of smooth layer film 36 for additional attraction between reusable leadwire adapter 14, 114 and disposable electrode 12. In addition, a wide variety of adhesives may be used to maintain the interface between reusable leadwire adapter 14, 114 and disposable electrode 12.

Figure 5:
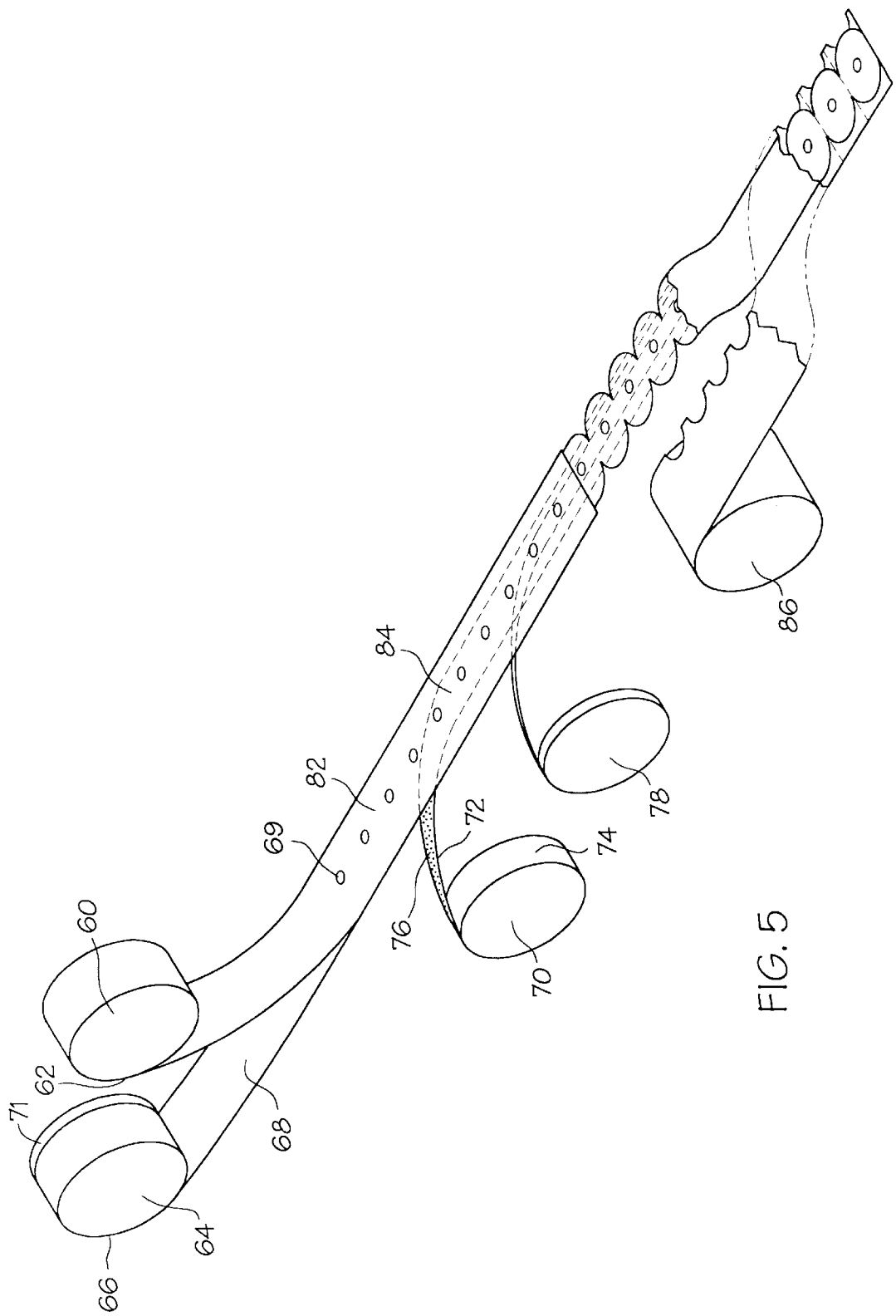
FIG. 5 is an exploded view of the manufacturing process of the disposable electrode according to the present invention.

FIG. 5 illustrates a method for manufacturing disposable electrode 12. A roll of smooth layer film 60 is provided having an adhesive 62 on the lower surface or side. A roll of top layer 64 is provided having an adhesive 66 on the upper surface or side. Smooth layer film 60 is applied to the lower surface 68 of top layer 64 by means of adhesive 62. A hole 69 is then punch in the center of the resulting combination at predetermined intervals. Preferably, top layer 66 includes a pull tab 71 on the lower surface.

An electrically conductive gel web 70 is provided having an electrically conductive gel layer 72 laminated to an anchoring layer 74 having perforated portion 76. Electrically conductive gel web 70 is applied to the lower surface of top layer 64 and by means of adhesive 66.

Preferably, an electrical stabilizing strip 78 is provided having an adhesive 80 on the lower surface or side. Electrical stabilizing strip is applied to the lower surface of electrically conductive gel web 70. Preferably, electrically conductive gel web 70 is applied to the center portion 82 of top layer 68 over hole 69. Electrical stabilizing strip 80 is preferably applied to the center portion 84 of gel web 70.

Figure 6:
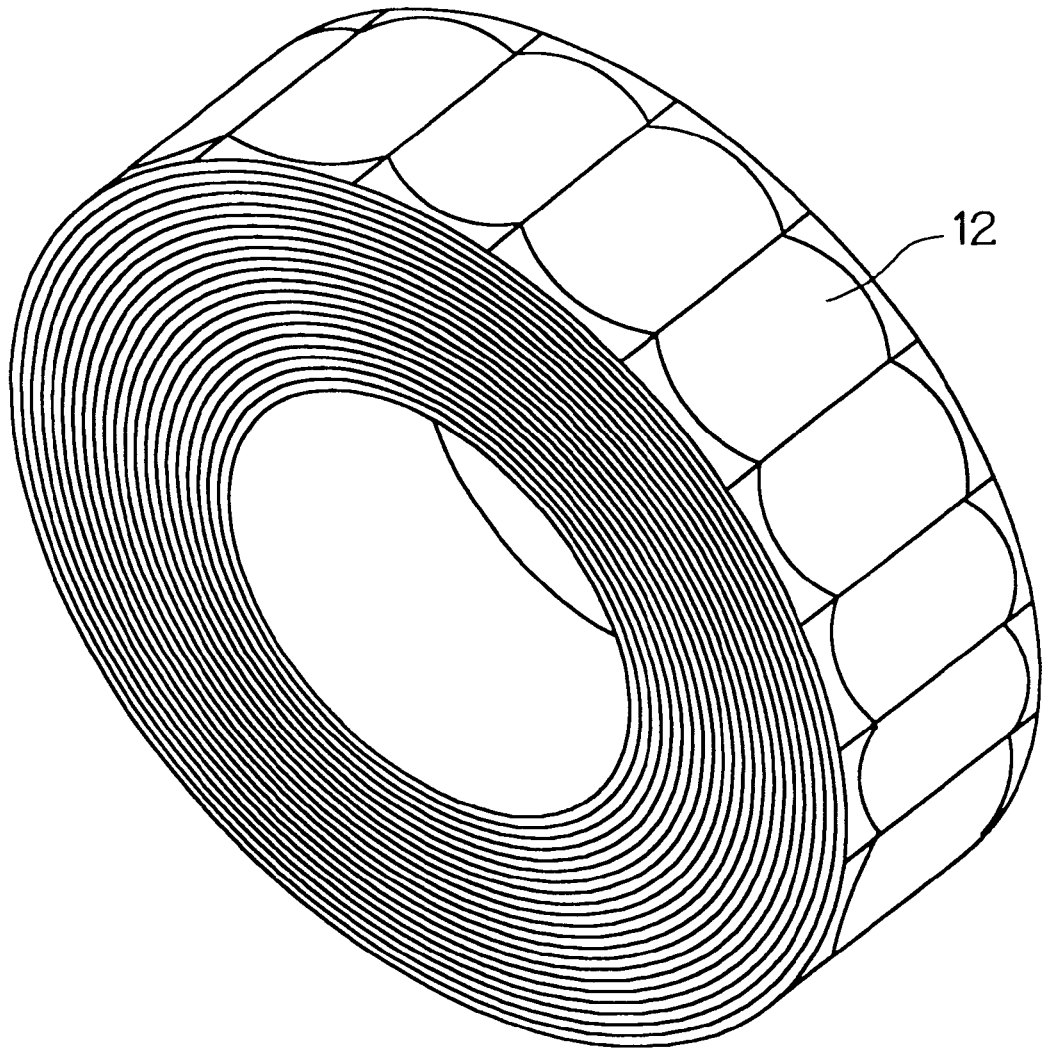
FIG. 6 is perspective view of a roll of disposable electrodes manufactured according to the present invention.

Preferably, the resultant combination is then cut to the desired oblong shape. A release liner 86 having the same top portion cut is provided and then applied to the lower surface of top layer 64, electrically conductive web 70 and electrical stabilizing strip 78. Finally, a separation cut is made such that the web is turned into individual disposable electrode and can be easily removed. The separation cut does not penetrate release liner 86 such that the web remains intact and individual electrodes may be removed as necessary. The resulting disposable electrodes 12 may be packaged as shown in FIG. 6 for ease of shipment, handling and storage. The above manufacturing materials are the same as the materials referenced above with respect to the disposable electrode 12.

Having described the invention in detail and by reference to preferred embodiments thereof, it will be apparent that modifications and variations are possible without departing from the scope of the invention which is defined in the appended claims.

What is claimed is:

1. A method of manufacturing a disposable electrode, comprising the steps of:

a) providing a smooth layer film having an upper side and a lower side, wherein said upper side and said lower side of said smooth layer film have an adhesive coating;

b) providing a top layer having an upper side and a lower side having an adhesive coating;

c) applying said lower side of said smooth layer film to said upper side of said top layer by means of said adhesive coating on said smooth layer film;

d) punching a hole in said smooth layer film and said top layer;

e) providing an electrically conductive gel web having an upper side and a lower side and comprising an electrically conductive gel layer and an anchoring layer formed of a porous material having sufficient porosity such that said anchoring layer is laminated on said electrically conductive gel layer; and f) applying said upper side of said electrically conductive web to said lower side of said top layer by means of said adhesive coating on said top layer.

2. The method of manufacturing the disposable electrode of claim 1, wherein said smooth layer film comprises a polyethylene material.

3. The method of manufacturing the disposable electrode of claim 1 wherein said lower side of said top layer includes a center portion and an outer portion, said electrically conductive patch is positioned over said center portion.

4. The method of manufacturing the disposable electrode of claim 1, wherein said electrically conductive gel layer comprises a hydrogel.

5. The method of manufacturing the disposable electrode of claim 1, further comprising the step of:

g) applying a release liner to said lower side of said top layer.

6. The method of manufacturing the disposable electrode of claim 5, wherein said lower side of said top layer has a pull tab, so as to provide a grippable surface to facilitate removal of said disposable electrode from said release liner.

7. The method of manufacturing the disposable electrode of claim 5, further comprising the step of:

h) making a separation cut between successive disposable electrodes.

8. The method of manufacturing the disposable electrode of claim 1, further comprising the step of:

g) cutting said disposable electrode to a desired shape.

9. A method of manufacturing a disposable electrode, comprising the steps of:

a) providing a smooth layer film having an upper side and a lower side having an adhesive coating;

b) providing a top layer having an upper side and a lower side having an adhesive coating;

c) applying said lower side of said smooth layer film to said upper side of said top layer by means of said adhesive coating on said smooth layer film;

d) punching a hole in said smooth layer film and said top layer;

e) providing an electrically conductive gel web having an upper side and a lower side, a center portion and an outer portion, and comprising an electrically conductive gel layer and an anchoring layer formed of a porous material having sufficient porosity such that said anchoring layer is laminated on said electrically conductive gel layer; wherein a perforated portion of said anchoring layer is positioned on said upper side and over said center portion of said electrically conductive gel web;

f) applying said upper side of said electrically conductive web to said lower side of said top layer by means of said adhesive coating on said top layer, g) providing an electrical stabilizing strip having an adhesive coating; and h) applying said electrical stabilizing strip to said lower side and over said center portion of said electrically conductive gel web by means of said adhesive coating on said electrical stabilizing strip.

10. The method of manufacturing the disposable electrode of is claim 9, wherein said electrical stabilizing strip is an insulator.

11. The method of manufacturing the disposable electrode of claim 10, wherein said insulator comprises a polyester material.

* * * * *